United States Patent [19]
Yokota

[11] Patent Number: 5,546,224
[45] Date of Patent: Aug. 13, 1996

[54] VIEWFINDER DEVICE WHEREIN THE SPACING BETWEEN THE DISPLAY AND THE OPTICAL SYSTEM IS VARIABLE TO EFFECT DIOPTER ADJUSTMENT

[75] Inventor: Hideo Yokota, Yokohama, Japan

[73] Assignee: Canon Kabushiki Kaisha, Tokyo, Japan

[21] Appl. No.: 348,220

[22] Filed: Nov. 28, 1994

[30] Foreign Application Priority Data

Nov. 29, 1993 [JP] Japan .................................. 5-298197

[51] Int. Cl.$^6$ .......................... G02B 23/00; G03B 13/36
[52] U.S. Cl. ...................... 359/425; 359/363; 359/400; 354/219; 354/222
[58] Field of Search ................... 359/362–363, 359/399, 407, 423, 432–435, 676, 808, 89, 424–425, 400; 354/219–225, 62; 351/208–211, 221

[56] References Cited

U.S. PATENT DOCUMENTS

| 4,982,278 | 1/1991 | Dahl et al. ................... | 359/407 |
| 5,257,055 | 10/1993 | Cho et al. ................... | 354/222 |
| 5,365,302 | 11/1994 | Kodama ....................... | 354/222 |

FOREIGN PATENT DOCUMENTS

| 0588290 | 3/1994 | European Pat. Off. . |
| 4300690 | 7/1993 | Germany . |
| 1-197727 | 8/1989 | Japan . |

OTHER PUBLICATIONS

Patent Abstracts of Japan, vol. 13, No. 495 (P–956) (3843), Nov. 11, 1989 (JP–A–1–197727, Aug. 9, 1989).

Primary Examiner—Thong Q. Nguyen
Attorney, Agent, or Firm—Fitzpatrick, Cella, Harper & Scinto

[57] ABSTRACT

A finder has a display for displaying an image, and a finder optical system for observing the image therethrough. The spacing between the display and the whole of the finder optical system is relatively varied to thereby effect the adjustment of the field of view.

6 Claims, 3 Drawing Sheets

VIEWFINDER DEVICE WHEREIN THE SPACING BETWEEN THE DISPLAY AND THE OPTICAL SYSTEM IS VARIABLE TO EFFECT DIOPTER ADJUSTMENT

BACKGROUND OF THE INVENTION

1. Field of the Invention

This invention relates to a finder for a video camera or the like, and particularly to a visual axis detecting finder for detecting a photographer's visual axis during operation of a camera.

2. Related Background Art

Cameras have been put on sale in which a focus position selected by a photographer is decided by detecting the photographer's visual axis have been put on sale.

A visual axis detecting apparatus is disclosed, for example, Japanese Laid-Open Patent Application No. 61-172,552. According to this publication, the center of pupil of a photographer's eye and the corneal reflected image (so-called Purkinje's image) of a light source for illuminating the eye are detected, and the direction to which the eye is directed is calculated from the relative relation between the Purkinje's image and the center of the pupil to thereby decide the direction of the visual axis.

Also, a finder in which visual axis detection and adjustment of the field of view of the finder are combined together is proposed, for example, in Japanese Laid-Open Patent Application No. 5-188,430.

This publication proposes a technique of moving some of the lenses constituting the eyepiece to effect diopter adjustment but so as not to affect visual axis detection in order to prevent any reduction in the accuracy of visual axis detection.

However, moving a part of the eyepiece in effecting diopter adjustment results in a variation of the size of the field of view and thus, an object in the field of view moves. Accordingly, when looking at a certain object, the visual axis deviates and it is necessary to detect the visual axis again. If a person's visual axis smoothly follows the object, it will be possible to detect the visual axis without so great a problem, but actually the visual axis may flicker or may sometimes move to different area. Particularly, in a finder of a high field magnification like an electronic viewfinder (EVF) in a video camera or the like, if a part of the eyepiece of the finder is moved, the variation in the field magnification will become great and the fluctuation of the visual axis will become great. Accordingly, in adjusting diopter, it is convenient to provide a finder which suffers little from a variation in the field magnification and in which the position of the object does not change.

SUMMARY OF THE INVENTION

In view of above-discussed problems, it is a first object of the present invention to provide a finder device which suffers little from a variation in field magnification in effecting diopter adjustment. It is a second object of the present invention to provide a finder device which can reduce the fluctuation of the visual axis and effect visual axis detection more accurately.

According to the present invention, a display means displays an image, and a finder optical system observes the image therethrough. Relatively varying the spacing between the display means and the whole of the finder optical system effects diopter adjustment.

DESCRIPTION OF THE PREFERRED EMBODIMENTS

Figure 1A:
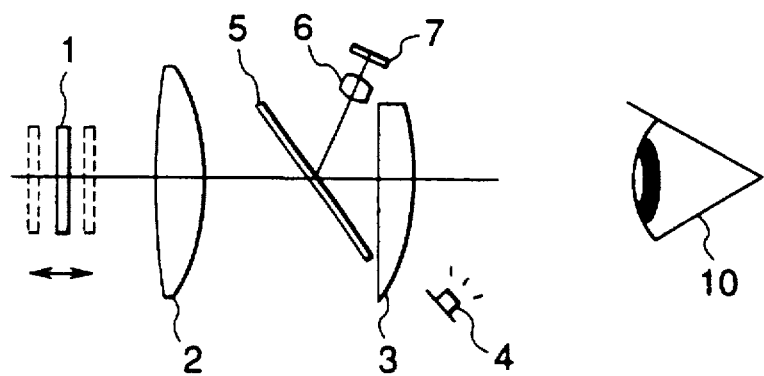
FIGS. 1A and 1B are side views of a finder according to a first embodiment of the present invention.
Figure 1B:
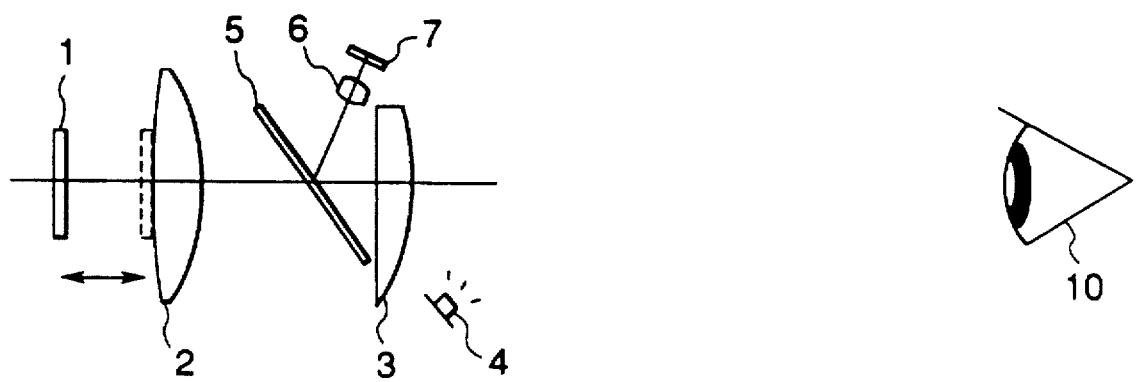

FIGS. 1A and 1B are side views of a finder device according to an embodiment of the present invention. The reference numeral 1 designates an image display element comprising a liquid crystal panel, a CRT or the like, the reference numerals 2 and 3 denote finder lenses for observing an image therethrough, and the reference numeral 4 designates an infrared light source such as a light emitting diode which emits infrared light of a wavelength longer than 680 mm. The reference numeral 5 denotes a dichroic mirror which reflects infrared light from an eye and transmits visible light therethrough. The reference numeral 6 designates an imaging lens for imaging an image of the eye, and the reference numeral 7 denotes an image pickup element such as a CCD for converting the image of the eye into an electrical signal. A conventional circuit, not shown, detects the visual axis of the eye on the basis of the output of the image pickup element 7. The finder lens 3, the lenses 2, 3, 6 (constituting the imaging lenses, the infrared light source 4, the dichroic mirror 5 and the image pickup element 7 are fixed to a finder housing, and the image display element 1 is made movable relative to the finder housing. An observer may look into the finder and move the position of the image display element 1 as by an external knob (not shown) to thereby effect diopter adjustment.

By doing this, the magnification of the finder is not varied and an object the observer is looking at does not move. Accordingly, there is no fluctuation of the visual axis and focus detection for a desired area can be accomplished stably. Also, if as shown in FIG. 1B, the image display element is designed to be able to be brought close to the finder lens side beyond the ordinary diopter adjustment range, it will be possible to create an observation state at a position in which the eye is kept apart from the finder.

Figure 4:
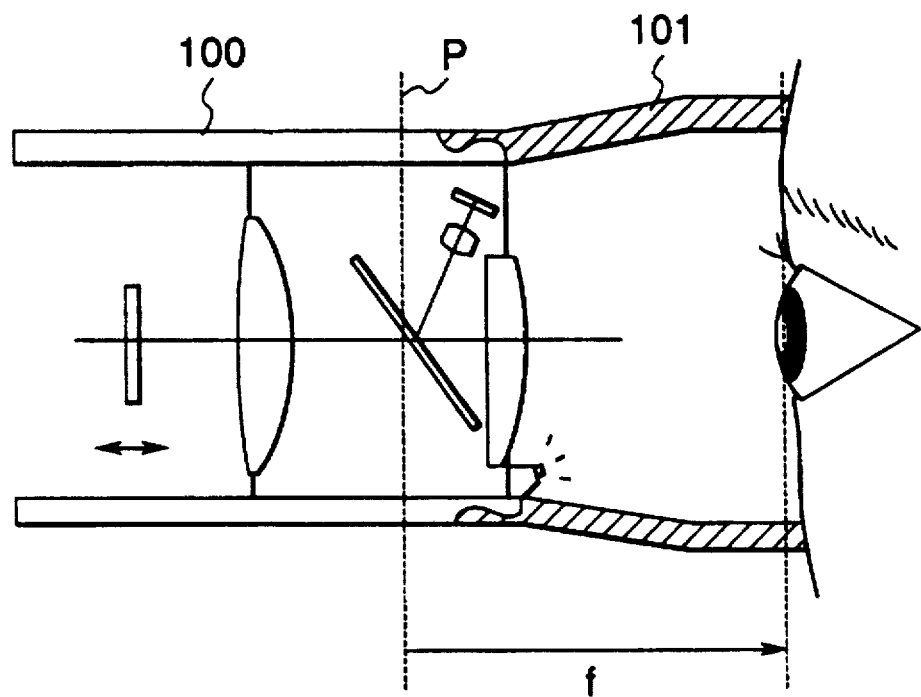
FIG. 4 illustrates an observation aiding member usable in the embodiments of the present invention.

Referring to FIG. 4 which shows the outer portion of the finder, the reference numeral 100 designates a finder housing and the reference numeral 101 denotes an observation aiding member such as an eye cap for aiding observation. The letter P indicates the eye side principal plane position of the whole finder lens, and the observation aiding member is set such that the eye (pupil) is placed near the eye side focus position of the finder lens (whose focal length is f). This is for the finder beam of light to maintain its telecentricity, and makes the fluctuation of the observer's angle of field by diopter adjustment small.

Figure 2:
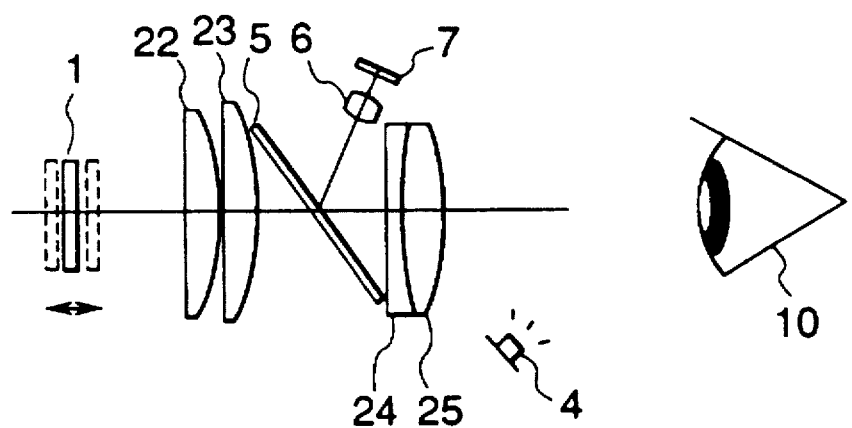
FIG. 2 is a side view of a finder according to a second embodiment of the present invention.

FIG. 2 shows a modification of the previous embodiment in which a finder lens is constituted by lenses 22, 23, 24 and 25, and the lenses 24 and 25 are made into a cemented lens comprising a concave lens and a convex lens so as to correct chromatic differences of magnification.

In the above-described embodiments, to correct distortion aberration, it is effective to use an aspherical lens as any of the lenses 2 and 3 of the finder lens or any of the lenses 22, 23, 24 and 25, and it is particularly effective to use an aspherical lens as the lens 2 or one (or both) of the lenses 22 and 23.

Figure 3:
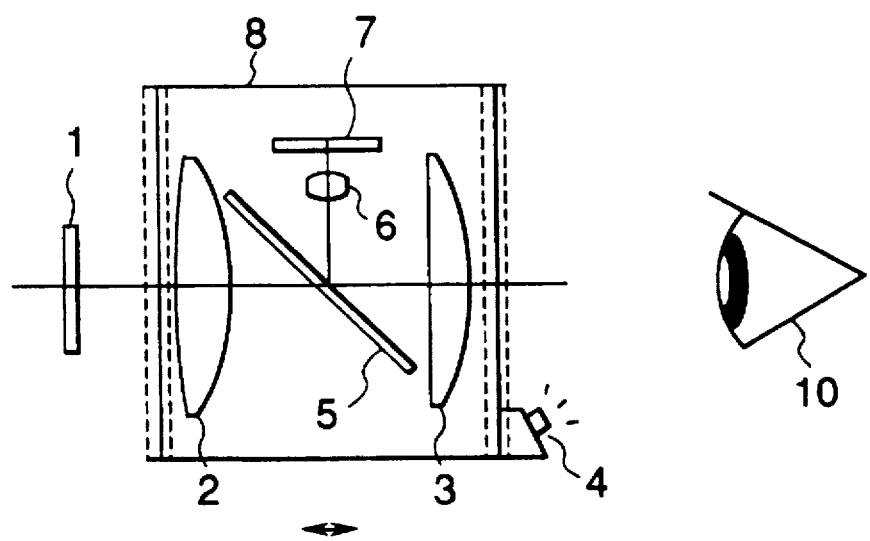
FIG. 3 is a side view of the finder according to yet another embodiment of the present invention.

Referring now to FIG. 3 which is a side view showing a further embodiment of the present invention, the reference numeral 1 designates an image display element fixed to a finder housing. The reference numeral 8 denotes a finder unit housing collectively holding finder lenses 2, 3, a light source 4, a dichroic mirror 5, an imaging lens 6 and an image pickup element 7 and movable relative to the finder housing. An observation aiding member (not shown) is fixed to the movable finder unit housing 8 so that the eye may move with the finder unit housing 8 when the latter is moved by diopter adjustment, whereby an effect similar to that of the previous embodiment can be provided.

Figure 5:
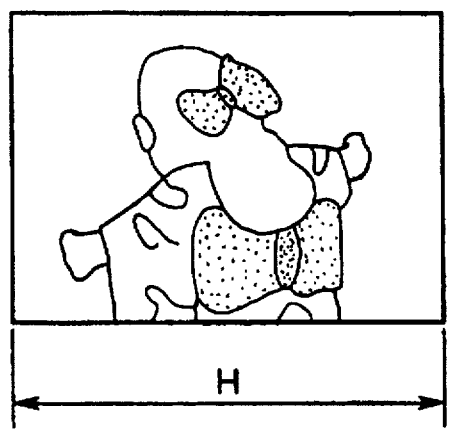
FIG. 5 shows an image display member.

Now, if the enlargement magnification of the image by the finder lens system is greater, the eye moves more greatly, and this is convenient for improving the detection accuracy of visual axis. To accomplish this, the focal length of the finder lens system may be shortened so as to satisfy the following relation:

H/f>0.37, where H is the size of image forming means in a horizontal direction (FIG. 5) and f is the focal length of the finder lens system constituting image observation means. In shortening the focal length, it is desirable to use a plurality of lenses and dispose a dichroic mirror in the spacing provided between the lenses.

Numerical value examples of the present invention will now be shown. In the numerical value examples below, Ri represents the radius of curvature of the ith lens surface as counted from the surface of the display element, Di represents the thickness and air space of the ith lens from the object side, and Ni and vi represent the refractive index and Abbe number, respectively, of the glass of the ith lens from the object side.

| Numerical Value Example 1 | | | |
|---|---|---|---|
| r | d | Nd | Vd |
| 1 | ∞ | 3.62 | 1.51633 | 64.2 |
| 2 | ∞ | 10.43 | 1 | |
| 3 | 150 | 4.60 | 1.50137 | 56.4 |
| 4 | −25.028 | 18.36 | 1 | |
| 5 | ∞ | 3.80 | 1.8313 | 59.4 |
| 6 | −29.193 | | | |

| focal length f | 30 |
|---|---|
| H | 14.2 |
| H/f | 0.47 |

| Numerical Value Example 2 | | | |
|---|---|---|---|
| r | d | Nd | Vd |
| 1 | ∞ | 3.62 | 1.51633 | 64.2 |
| 2 | ∞ | 7.24 | 1 | |
| 3 | ∞ | 3.2 | 1.49171 | 57.4 |
| 4 | −23.633 | 0.2 | 1 | |
| 5 | 187.5 | 3.3 | 1.49171 | 57.4 |
| 6 | −25.029 | 12.12 | 1 | |
| 7 | ∞ | 1.3 | 1.84666 | 23.8 |
| 8 | 47.15 | 3.9 | 1.62299 | 58.2 |
| 9 | 25.44 | | | |

| focal length f | 21 |
|---|---|
| H | 8.8 |
| H/f | 0.42 |

By the present invention, accurate detection of the visual axis becomes always possible even when observers of different diopters observe the finder.

As described above, the finder of the present invention is particularly suitable as the finder of a video camera or the like which is considered to be used by various persons, and it becomes possible to improve greatly the operation during photographing using visual axis detection.

What is claimed is:

1. A finder device including:

display means for displaying an image; and a finder optical system for observing said image therethrough, a spacing between said display means and said finder optical system being variable to effect diopter adjustment, said display means and said finder optical system being disposed to satisfy the following condition:

H/f>0.37, where H is the length of said display means in a horizontal direction, and f is the focal length of said finder optical system.

2. A finder device according to claim 1, wherein said finder optical system has a plurality of lenses and a reflecting member disposed between said lenses for reflecting light from an eye, and a sensor for receiving the light reflected from said reflecting member.

3. A device according to claim 1, wherein said display means is movable to effect diopter adjustment.

4. A finder device comprising:

display means for displaying an image;

an eyepiece lens unit for transmitting the displayed image to an eye of an observer;

an illumination unit for illuminating the eye;

a light receiving unit for receiving light reflected from the eye; and a housing for housing said eyepiece lens unit, said illumination unit, and said light receiving unit, said display means being movable with respect to said housing for effecting diopter adjustment.

5. A device according to claim 4, wherein said display means and said eyepiece lens unit satisfy the following condition:

H/f>0.37 where H is a length of said display means in a horizontal direction, and f is a focal length of said eyepiece lens unit.

6. A device according to claim 4, wherein said eyepiece lens unit further comprises a plurality of lenses and a light splitting member disposed between said lenses.

* * * * *

UNITED STATES PATENT AND TRADEMARK OFFICE
CERTIFICATE OF CORRECTION

PATENT NO. : 5,546,224
DATED : August 13, 1996
INVENTOR(S) : HIDEO YOKOTA

It is certified that error appears in the above-indentified patent and that said Letters Patent is hereby corrected as shown below:

<u>Column 1</u>,
    line 18, "axis have been put on sale." should read --axis.--;
    line 21, "61-172,522." should read --61-172522.--; and
    line 45, "different" should read --a different--.

Signed and Sealed this

Fourth Day of February, 199'

Attest:

BRUCE LEHMAN

*Attesting Officer*      *Commissioner of Patents and Trademarks*